(12) United States Patent
Stahmann et al.

(10) Patent No.: US 8,630,718 B2
(45) Date of Patent: Jan. 14, 2014

(54) INSULATIVE STRUCTURE FOR MRI COMPATIBLE LEADS

(75) Inventors: Jeffrey E. Stahmann, Ramsey, MN (US); Scott R. Stubbs, Maple Grove, MN (US); Arthur J. Foster, Centerville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 68 days.

(21) Appl. No.: 13/239,629

(22) Filed: Sep. 22, 2011

(65) Prior Publication Data

US 2012/0130453 A1 May 24, 2012

Related U.S. Application Data

(60) Provisional application No. 61/414,975, filed on Nov. 18, 2010.

(51) Int. Cl.
*A61N 1/05* (2006.01)

(52) U.S. Cl.
USPC .......................................... 607/115

(58) Field of Classification Search
USPC .................................. 607/115–122
See application file for complete search history.

(56) References Cited

U.S. PATENT DOCUMENTS

| 4,131,759 | A | 12/1978 | Felkel |
| 4,484,586 | A | 11/1984 | McMickle et al. |
| 5,554,139 | A | 9/1996 | Okajima |
| 5,800,496 | A | 9/1998 | Swoyer et al. |
| 6,143,013 | A | 11/2000 | Samson et al. |
| 6,671,554 | B2 | 12/2003 | Gibson et al. |
| 6,876,886 | B1 * | 4/2005 | Wang .............................. 607/119 |
| 6,980,865 | B1 * | 12/2005 | Wang et al. .................... 607/121 |
| 7,013,180 | B2 | 3/2006 | Dublin et al. |
| 7,015,392 | B1 | 3/2006 | Dickenson |
| 7,123,013 | B2 | 10/2006 | Gray |
| 7,138,582 | B2 | 11/2006 | Lessar et al. |
| 7,174,219 | B2 | 2/2007 | Wahlstrand et al. |
| 7,174,220 | B1 | 2/2007 | Chitre et al. |
| 7,388,378 | B2 | 6/2008 | Gray et al. |
| 7,410,485 | B1 | 8/2008 | Fink et al. |
| 7,551,966 | B2 * | 6/2009 | MacDonald ................... 607/119 |

(Continued)

FOREIGN PATENT DOCUMENTS

| EP | 0092798 A1 | 11/1983 |
| JP | 58192205 A | 11/1983 |

(Continued)

OTHER PUBLICATIONS

International Search Report and Written Opinion issued in PCT/US2011/052684, mailed Jan. 25, 2012, 11 pages.

(Continued)

*Primary Examiner* — Brian T Gedeon
(74) *Attorney, Agent, or Firm* — Faegre Baker Daniels LLP

(57) ABSTRACT

A medical device lead includes a proximal connector, an insulative lead body extending distally from the proximal connector. The proximal connector is configured to couple the lead to a pulse generator. A first conductive coil is coupled to the proximal connector and extends through the lead body. The first conductive coil is coupled to a first electrode at a distal end of the first conductive coil. A first magnetically impregnated polymer layer is adjacent the first conductive coil.

20 Claims, 4 Drawing Sheets

(56) References Cited

U.S. PATENT DOCUMENTS

| | | |
|---|---|---|
| 8,244,346 B2 * | 8/2012 | Foster et al. .................. 607/2 |
| 8,275,464 B2 | 9/2012 | Li et al. |
| 2003/0014080 A1 | 1/2003 | Baudino |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144705 A1 | 7/2003 | Funke |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0162600 A1 | 8/2004 | Williams |
| 2004/0210289 A1 | 10/2004 | Wang et al. |
| 2005/0065587 A1 | 3/2005 | Gryzwa |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0247472 A1 | 11/2005 | Helfer et al. |
| 2005/0283167 A1 | 12/2005 | Gray |
| 2006/0030774 A1 | 2/2006 | Gray et al. |
| 2006/0041294 A1 | 2/2006 | Gray |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2007/0106332 A1 | 5/2007 | Denker et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2008/0033497 A1 | 2/2008 | Bulkes et al. |
| 2008/0132985 A1 | 6/2008 | Wedan et al. |
| 2008/0195186 A1 | 8/2008 | Li et al. |
| 2009/0149920 A1 | 6/2009 | Li et al. |
| 2009/0149934 A1 | 6/2009 | Ameri et al. |
| 2009/0171421 A1 | 7/2009 | Atalar et al. |
| 2010/0036466 A1 | 2/2010 | Min et al. |
| 2012/0130453 A1 | 5/2012 | Stahmann et al. |
| 2012/0323297 A1 | 12/2012 | Li et al. |

FOREIGN PATENT DOCUMENTS

| | | |
|---|---|---|
| JP | 8308934 A | 11/1996 |
| JP | 2003047653 A | 2/2003 |
| JP | 2004141679 A | 5/2004 |
| JP | 2005515854 A | 6/2005 |
| WO | WO2005081784 A2 | 9/2005 |
| WO | WO2007047966 A2 | 4/2007 |

OTHER PUBLICATIONS

International Search Report and Written Opinion issued in PCT/US2008/085518 on Oct. 29, 2009, 15 pages.

International Search Report and Written Opinion issued in PCT/US2008/085533, mailed Aug. 26, 2010.

International Search Report and Written Opinion issued in PCT/US2008/087068 on Aug. 3, 2009.

Invitation to Pay Additional Fees and Partial Search Report, dated Aug. 17, 2009, issued in PCT/US2008085533, 6 pages.

* cited by examiner

INSULATIVE STRUCTURE FOR MRI COMPATIBLE LEADS

CROSS-REFERENCE TO RELATED APPLICATION

This application claims priority to Provisional Application No. 61/414,975, filed Nov. 18, 2010, which is herein incorporated by reference in its entirety.

TECHNICAL FIELD

The present invention relates to implantable medical devices. More particularly, the present invention relates to a medical device lead including an insulative structure including magnetic particles.

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic or electromagnetic fields may also induce an undesired voltage on the lead or result in an inability to sense physiological signals from the lead electrodes or sensors.

SUMMARY

Discussed herein are insulative structures for implantable medical electrical leads including insulative layers impregnated with magnetic materials (referred to herein as "magnetically impregnated"), as well as medical electrical leads including such insulative structures.

In Example 1, a medical device lead includes a proximal end and an insulative lead body extending distally from the proximal end. The proximal end is configured to couple the lead to a medical device. A first conductor is coupled to the proximal end and extends through the lead body. The first conductor is coupled to a first electrode at a distal end of the first conductor. A first magnetically impregnated polymer layer is adjacent the first conductor.

In Example 2, the medical device lead according to Example 1, and further comprising a second conductor coupled to the proximal end and extending coaxially or co-radially with the first conductor. The second conductor is coupled to a second electrode at a distal end of the second conductor. A second magnetically impregnated insulative layer is adjacent the first conductor.

In Example 3, the medical device lead according to either Example 1 or 2, wherein the first conductor comprises a conductive coil.

In Example 4, the medical device lead according to any of Examples 1-3, and further comprising a first non-magnetically impregnated insulative layer between the first magnetically impregnated insulative layer and the first conductor and a second non-magnetically impregnated insulative layer on a side of the first conductor opposite the first non-magnetically impregnated insulative layer.

In Example 5, the medical device lead according to any of Examples 1-4, wherein a percentage of magnetic material in the first magnetically impregnated insulative layer is less than or equal to about 10%.

In Example 6, the medical device lead according to any of Examples 1-5, wherein the first magnetically impregnated insulative layer comprises particles of magnetic material having varying sizes and/or varying shapes.

In Example 7, the medical device lead according to any of Examples 1-6, wherein the particles of magnetic material are nanoparticles.

In Example 8, the medical device lead according to any of Examples 1-7, wherein the first magnetically impregnated insulative layer comprises magnetically impregnated sections spaced apart by non-magnetically impregnated sections that provide impedance discontinuities in the first magnetically impregnated insulative layer.

In Example 9, a medical device lead includes an insulative lead body, a first lead conductor extending through the lead body, and a first magnetically impregnated insulative layer between the first lead conductor and a central lumen of the medical device lead. The first lead conductor is coupled to a first electrode at a distal end of the first lead conductor.

In Example 10, the medical device lead according to Example 9, and further comprising a first non-magnetically impregnated insulative layer between the first magnetically impregnated insulative layer and the central lumen, and a second non-magnetically impregnated insulative layer between the first lead conductor and the first magnetically impregnated insulative layer.

In Example 11, the medical device lead according to either Example 9 or 10, and further comprising a second lead conductor extending coaxially or co-radially with the first lead conductor, the second lead conductor coupled to a second electrode at a distal end of the second lead conductor.

In Example 12, the medical device lead according to any of Examples 9-11, and further comprising a second magnetically impregnated insulative layer between the first lead conductor and the second non-magnetically impregnated insulative layer.

In Example 13, the medical device lead according to any of Examples 9-12, and further comprising a third non-magnetically impregnated insulative layer between the first lead conductor and the second magnetically impregnated insulative layer, and a fourth non-magnetically impregnated insulative layer between the second magnetically impregnated insulative layer and the second lead conductor.

In Example 14, the medical device lead according to any of Examples 9-13, wherein the first magnetically impregnated insulative layer comprises particles of magnetic material.

In Example 15, the medical device lead according to any of Examples 9-14, wherein the particles of magnetic material are substantially spherical.

In Example 16, the medical device lead according to any of Examples 9-15, wherein the particles of magnetic material have varying sizes and/or varying shapes.

In Example 17, the medical device lead according to any of Examples 9-16, wherein the first magnetically impregnated insulative layer comprises magnetically impregnated sections spaced apart by non-magnetically impregnated sections that provide impedance discontinuities in the first magnetically impregnated insulative layer.

In Example 18, a medical device includes a pulse generator and a lead couplable to the pulse generator. The lead includes a lead body, an outer conductive coil extending through the lead body, and an inner conductive coil extending coaxially with the outer conductive coil. The lead further includes a first insulative layer between the inner conductive coil and a central lumen of the lead, and a second insulative layer between the inner conductive coil and outer conductive coil. At least one of the first and second insulative layers includes a magnetic material.

In Example 19, the medical device according to Example 18, wherein the lead further comprises a third insulative layer between the first insulative layer and the central lumen, and a fourth insulative layer between the inner conductive coil and the first insulative layer.

In Example 20, the medical device according to either Example 18 or 19, wherein the lead further comprises a fifth insulative layer between the first lead conductor and the second insulative layer, and a sixth insulative layer between the second insulative layer and the second lead conductor.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
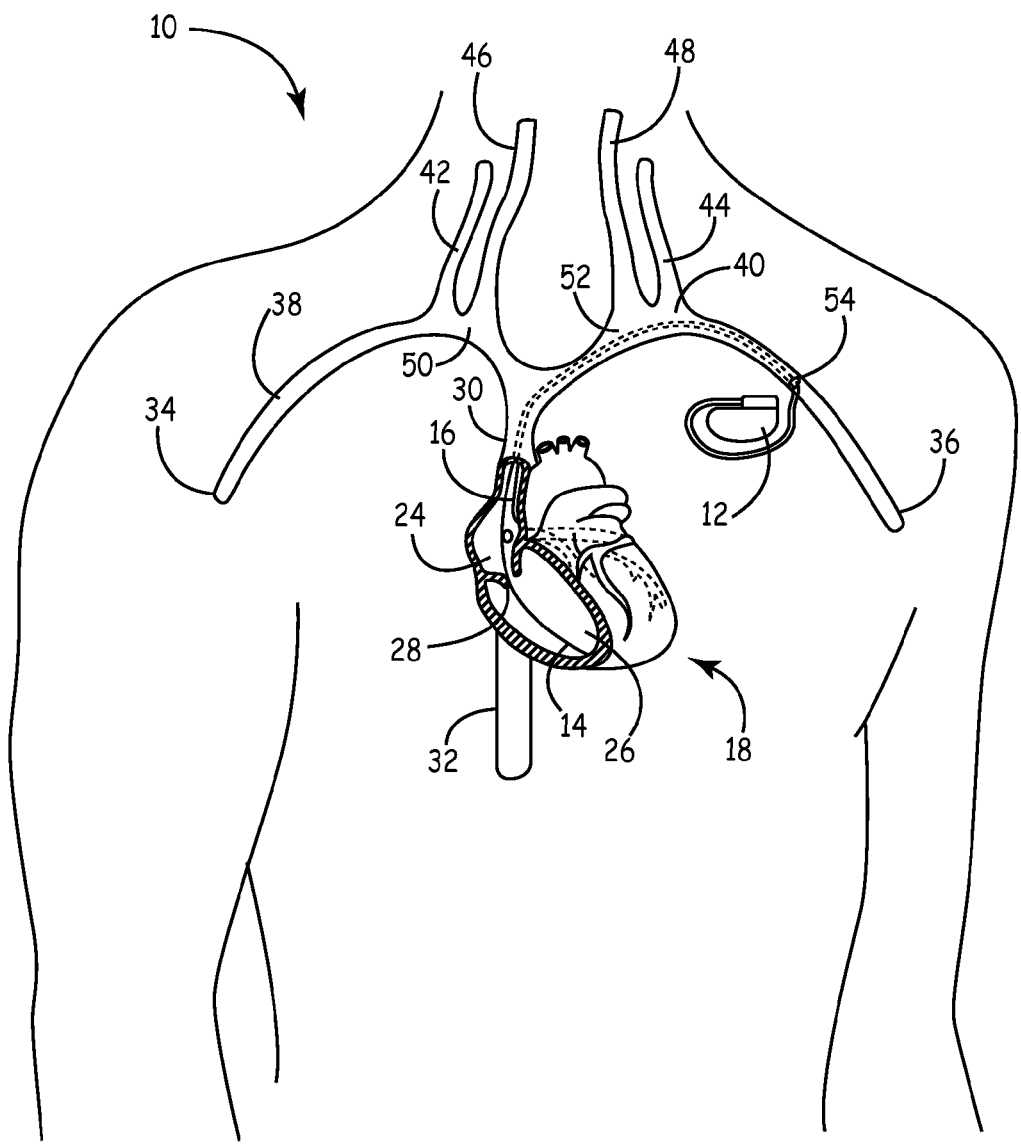
FIG. 1 is a schematic view of a cardiac rhythm management (CRM) system including a pulse generator and a lead implanted in a patient's heart according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management (CRM) system 10 according to an embodiment of the present invention. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. The major veins supplying blood to the superior vena cava 30 include the right and left axillary veins 34 and 36, which flow into the right and left subclavian veins 38 and 40. The right and left external jugular 42 and 44, along with the right and left internal jugular 46 and 48, join the right and left subclavian veins 38 and 40 to form the right and left brachiocephalic veins 50 and 52, which in turn combine to flow into the superior vena cava 30.

The leads 14, 16 operate to convey electrical signals and stimuli between the heart 18 and the pulse generator 12. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy system. As shown, the leads 14, 16 enter the vascular system through a vascular entry site 54 formed in the wall of the left subclavian vein 40, extend through the left brachiocephalic vein 52 and the superior vena cava 30, and are implanted in the right ventricle 26 and right atrium 24, respectively. In other embodiments of the present disclosure, the leads 14, 16 may enter the vascular system through the right subclavian vein 38, the left axillary vein 36, the left external jugular 44, the left internal jugular 48, or the left brachiocephalic vein 52.

The pulse generator 12 is typically implanted subcutaneously within an implantation location or pocket in the patient's chest or abdomen. The pulse generator 12 may be an implantable medical device known in the art or later developed, for delivering an electrical therapeutic stimulus to the patient. In various embodiments, the pulse generator 12 is a pacemaker, an implantable cardiac defibrillator, a cardiac resynchronizer, and/or includes both stimulation and defibrillation capabilities. Yet other embodiments include neurostimulators or devices providing diagnostic but no therapeutic capability. The portion of the leads 14, 16 extending from the pulse generator 12 to the vascular entry site 54 are also located subcutaneously or submuscularly. The leads 14, 16 are each connected to the pulse generator 12 via proximal connectors. Any excess lead length, i.e., length beyond that needed to reach from the pulse generator 12 location to the desired endocardial or epicardial implantation site, is generally coiled up in the subcutaneous pocket near the pulse generator 12.

The electrical signals and stimuli conveyed by the pulse generator 12 are carried to electrodes at the distal ends of leads 14, 16 by one or more conductors extending through the leads 14, 16. The one or more conductors are each electrically coupled to a connector suitable for interfacing with the pulse generator 12 at the proximal end of the leads 14, 16 and to one or more electrodes at the distal end. In an MRI environment, the electromagnetic radiation produced by the MRI system may be picked up by conductors of the leads 14, 16. This energy may be transferred through the leads 14, 16 to the electrode in contact with the tissue, which may lead to elevated temperatures at the point of contact. The present disclosure relates to insulative structures in at least one of the leads 14, 16 that include magnetic particles (i.e., magnetically impregnated insulators) to increase the self inductance of the one or more lead conductors. Increasing the inductance of the lead decreases the RF energy absorbed by the lead 14, 16, thereby reducing or eliminating heating at the electrode/tissue interface.

Figure 2:
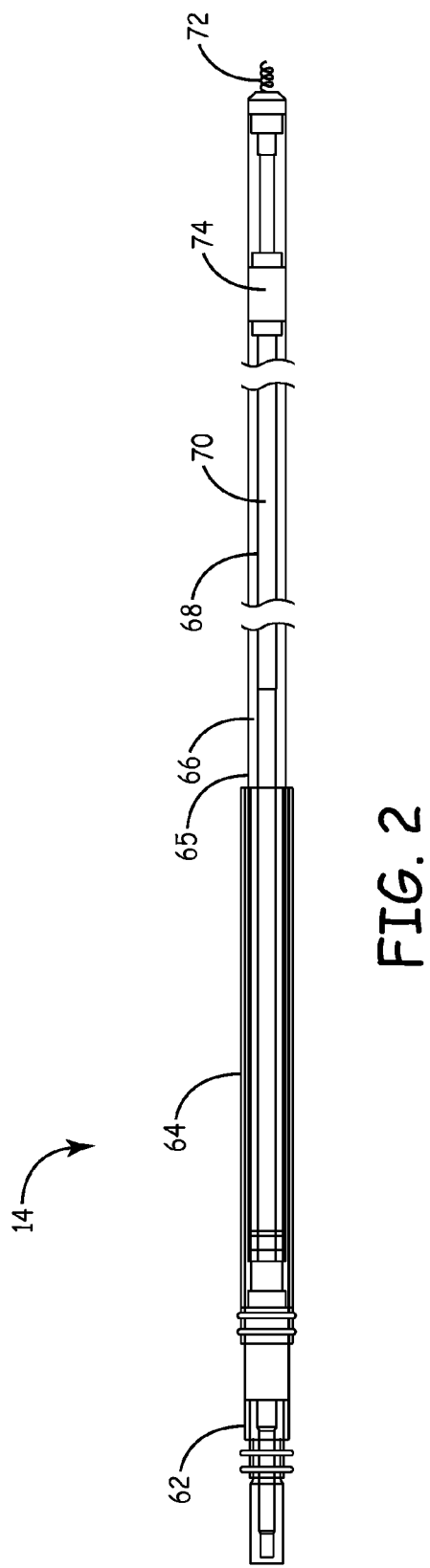
FIG. 2 is a side view of a lead suitable for use with the CRM system shown in FIG. 1.

FIG. 2 is a side view of a lead 14 that may be suitable for use with the CRM system 10 shown in FIG. 1. While the lead 14 is shown, the lead 16 may have a similar construction. The lead 14 includes a proximal connector 62, an insulative lead body 64, an outer magnetically impregnated insulative layer 65, an outer conductive coil 66, an inner magnetically impregnated insulative layer 68, and an inner conductive coil 70. In some embodiments, the inner conductive coil 70 is a co-radial or coaxial assembly of coils that extends from the connector 62 at the proximal end of the lead 14 to one or more electrodes 72 at the distal end of the lead 14. The outer conductive coil 66 extends coaxially with the inner conductive coil 70 and is electrically isolated from the inner conductive coil 70 by the insulative layer 68. The outer conductive coil 66 is connected to the connector 62 at the proximal end of the lead 14 and to one or more electrodes 74 at the distal end of the lead 14. The insulative lead body 64 surrounds the outer magnetically impregnated insulative layer 65 and supports the one or more electrodes 72, 74 electrically coupled to distal ends of the inner conductive coil 70 and outer conductive coil 66, respectively. The connector 62 is configured to couple to the pulse generator 12 (FIG. 1) and electrically connects the electrodes 72, 74 to the pulse generator 12 via the inner conductive coil 70 and outer conductive coil 66, respectively. The electrodes 72, 74 are merely illustrative, and may be configured for use in pacing, sensing, heart failure, neurostimulation, diagnostic, and/or shock therapy applications. In addition, while active fixation electrode 72 is shown, the electrode 72 may alternatively be configured for passive fixation of the lead 14 to tissue of the heart 18, or without a fixation mechanism.

Figure 3:
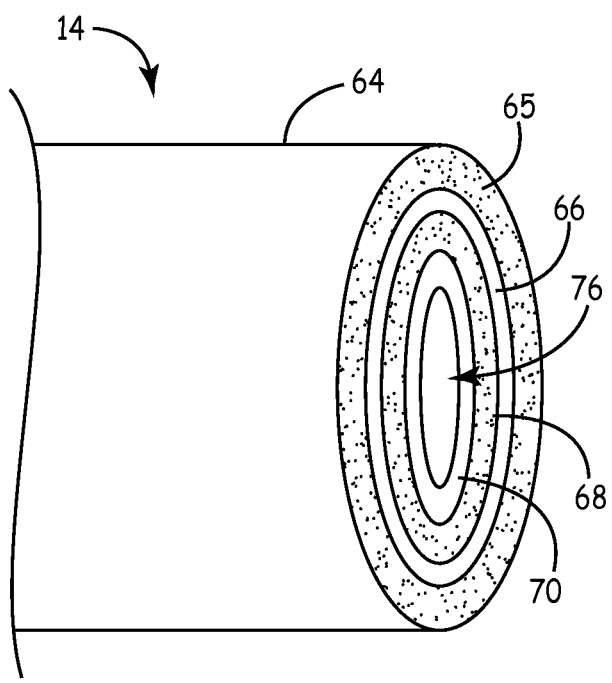
FIG. 3 is a cutaway view of a portion of an embodiment of a lead including magnetically impregnated insulative layers.

FIG. 3 is a cutaway side view of a portion of the lead 14 showing the interior construction of the distal end of the lead 14 in accordance with an exemplary embodiment. As discussed above, the lead 14 includes an insulative lead body 64, an outer magnetically impregnated insulative layer 65, an outer conductive coil 66, an inner magnetically impregnated insulative layer 68, and an inner conductive coil 70. The inner magnetically impregnated insulation layer 68 is disposed between the outer conductive coil 66 and inner conductive coil 70, and the outer magnetically impregnated insulation layer 65 is between the lead body 64 and the outer conductive coil 66. The inner conductive coil 70 defines an inner lumen 76 through a center of the lead 14. In alternative embodiments, the inner conductive coil 70 and outer conductive coil 66 can have other configurations, such as a conductive cable, and/or the insulative layers 65, 68 may be disposed inside of the conductive coils 66, 70, respectively.

In the embodiment illustrated in FIG. 3, the inner conductive coil 70 comprises a helically-shaped conductive coil including one or more filars that are tightly wound together to form an inner conductor used to deliver electrical stimulus energy through the lead 14. In one embodiment, for example, the inner conductive coil 70 comprises a single filar. In other embodiments, the inner conductive coil 70 can include a greater number of filar strands. In some embodiments, each of the filar strands forming the inner conductive coil 70 can comprise a silver-filled MP35N wire having a silver content of about 10% to about 50% by cross-sectional area. In certain embodiments, the pitch of the inner conductive coil 70 is about one to one and a half times the filar diameter of the inner conductive coil 70.

In some embodiments, the inner conductive coil 70 has a hollowed configuration, including an interior lumen 76 extending through the inner conductive coil 70 and adapted to receive a stylet or guidewire that can be used to facilitate implantation of the lead 14 within the body. In certain embodiments, the inner conductive coil 70 can be fabricated by co-radially winding a number of wire filars about a mandrel having a diameter that is slightly greater than the diameter of the stylet or guidewire to be inserted into the lumen 76. To improve the torque characteristics of the coil 70, the wire filars can be tightly wound together during fabrication of the coil 70 such that no gaps or spaces exist between the filar strands.

As further shown in FIG. 3, and in some embodiments, the outer conductive coil 66 is coaxially disposed about the inner conductive coil 70 and has a helically coiled configuration that extends along all or a portion of the length of the lead 14. In some embodiments, the outer conductive coil 66 has a single-filar construction formed from a single wound wire. In other embodiments, the outer conductive coil 66 has a multifilar construction formed from multiple, co-radially wound wire filars. In one embodiment, for example, the outer conductive coil 66 has a double-filar construction formed from two co-radially wound wire filars.

The outer conductive coil 66 can be spaced radially apart from the inner conductive coil 70, electrically isolating the outer conductive coil 66 from the inner conductive coil 70. In some embodiments, for example, the outer conductive coil 66 is electrically isolated from the inner conductive coil 70 so that the lead 14 can function as a multipolar lead. In certain embodiments, the inner magnetically impregnated insulative layer 68 interposed between the inner conductive coil 70 and the outer conductive coil 66 is further used to electrically isolate the conductive coils 66, 70 from each other. In some embodiments, for example, the insulative layer 68 may comprise a sheath made from silicon, polyurethane, or other suitable polymeric material.

In some embodiments, the outer conductive coil 66 is formed from a drawn-filled tube having an outer tubular layer of low-resistive metal or metal-alloy such as MP35N filled with an inner core of electrically conductive material such as silver. Once filled and drawn, the tube is then coiled into a helical shape and attached to the lead 14 using conventional techniques known in the art. In one embodiment, the outer conductive coil 66 comprises a silver-filled MP35N wire having a silver content of about 28% by cross-sectional area. In use, the relatively low resistance of the outer tubular metal or metal-alloy forming part of the outer conductive coil 66 can be used to offset the increased resistance imparted to the conductive coil 66 from using a smaller diameter wire, as discussed above. In some embodiments, the material or materials forming the outer conductive coil 66 can also be selected so as to impart greater flexibility to the conductive coil 66.

The outer conductive coil 66 may be formed from a material or materials different than the inner conductive coil 70 in order to impart greater resistance to the outer conductive coil 66 to aid in dissipating RF electromagnetic energy received during an MRI procedure. In one embodiment, for example, the wire filars forming the outer conductive coil 66 may comprise a silver-filled MP35N material having a silver content (by cross-sectional area) of about 28%, whereas the wire filars forming the inner conductive coil 70 may have a silver content (by cross-sectional area) lower than 28%.

The outer conductive coil 66 is coupled to proximal electrode 74 at a distal end of the outer conductive coil 66, and the inner conductive coil 70 is coupled to distal electrode 72 at a distal end of the inner conductive coil 70. In the embodiment shown, the electrode 74 is a ring electrode and the electrode 72 is an active fixation helix electrode that is coupled to the tissue of the heart 18 upon implantation. It will be appreciated, however, that the electrodes 72, 74 can have other configurations. For example, the electrode 72 may be a tip electrode without a fixation mechanism. In other embodiments, the lead 14 can be configured with more or fewer electrodes.

According to various embodiments, one or both of the insulative layers 65, 68 are impregnated with a magnetic material to increase the self inductance of the conductive coils 66, 70. That is, the insulative layers 65, 68 include an insulative material interspersed with or otherwise including a magnetic material. Increasing the inductance of the lead 14 improves the ability of the lead 14 to reject RF energy during MRI scans in that the increased inductance reduces RF energy absorption by the lead 14. In some embodiments, the insulative layers 65, 68 are comprised of a polymeric material. The inductance L of the lead 14 can be approximated as:

$$L = \frac{\mu_0 \mu_r A N^2}{d}, \qquad (1)$$

where A is the cross-sectional area of the conductive coils, d is the length of the lead 14, $\mu_r$ and $\mu_0$ are the relative permeability of the core of the lead 14 and the permeability of free space, respectively, and N is the number of turns of the conductive coil 66 or 70. Impregnating one or both of the insulative layers 65, 68 with magnetic material increases relative permeability of the core of the lead 14, thereby increasing the inductance of the lead 14.

The insulative layers 65, 68 may be impregnated with magnetic particles. The magnetic particles may have substantially uniform size, or the magnetic particles may have varying sizes. The magnetic particles may be in the form of a powdered ferromagnetic material. In some embodiments, the magnetic particles may be substantially spherical. In other embodiments, the magnetic particles may have other shapes, such as oval, ribbons, or polyhedral. In some embodiments, the magnetic particles may be comprised of a nanomagnetic material. In some embodiments, the magnetic material may be mixed or otherwise introduced into the insulative material of insulative layers 65, 68 and formed in the lead 14, such as by molding, extrusion, dye processing, or sheet casting.

The magnetic properties (e.g., relative permeability ($\mu_r$), saturation magnetization ($B_{sat}$)) of magnetic materials can be dependent on the size and geometry of the magnetic specimen. Thus, the size and geometry of the magnetic particles used to impregnate the insulative layers 65, 68 may be configured to ensure the magnetic properties of the impregnating magnetic material are capable of creating the desired effects within the lead 14. In some embodiments, a minimum diameter of spherical particles of magnetic material is greater than about 0.5 mm. In some embodiments, a minimum length of an elongated particle is about 10 mm.

The amount of magnetic material in the magnetically impregnated insulative layers 65, 68 may be varied along the length of the insulative layers 65, 68. In some embodiments, the insulative layers 65 and/or 68 include lengths or portions that are non-magnetically impregnated that separate magnetically impregnated lengths or portions. The non-magnetically impregnated portions may be arranged periodically along the length of the insulative layers 65 and/or 68. In some embodiments, the length of the magnetically impregnated portions is varied to change the RF resonant length of the lead 14. This introduces impedance discontinuities in the insulative layers 65, 68, which reduces the energy picked up by the lead 14 in an MRI environment.

In some embodiments, the magnetic material used to impregnate the insulative layers 65, 68 has a $\mu_r$ of at least about 10 and a $B_{sat}$ of at least about 0.2 T. In addition, since it is desirable to dissipate as much energy within the lead 14 as possible, the magnetic material may also have a large coercivity. Examples of magnetic materials that have a sufficiently high $B_{sat}$ and $\mu_r$ for use in the magnetically impregnated insulative layers 65, 68 include, but are not limited to, Fe, FeCo, silicon iron, carbon steel, nanoparticles, FeNi, Co, AlNiCo 2C, Ni, ferrites, permalloy, polymer composite films, Mu-metal, and combinations thereof.

The amount of magnetic material in the magnetically impregnated insulative layers 65, 68 can have an effect on the ability of the lead 14 to reject RF energy, as well as the mechanical and insulative properties of the insulative layers 65, 68. In addition, the amount of magnetic material in the insulative layers 65, 68 can also affect the force imparted by the lead 14 on surrounding tissue due to the static or gradient magnetic fields produced by the MRI scanner. In some embodiments, the percentage by volume of magnetic material in the insulative layers 65, 68 is less than or equal to about 10%. In other embodiments, the percentage of magnetic material by volume in the insulative layers 65, 68 is less than or equal to about 25%. The percentage of magnetic material in the insulative layers 65, 68 may be a function of the relative permeability, size, and/or shape of the magnetic material incorporated in the insulative layers 65, 68. In addition, with increased magnetic material in the insulative layers 65, 68, it may be desirable to include non-magnetically impregnated insulative layers around the magnetically impregnated insulative layers 65, 68, as discussed herein in the embodiment shown in FIGS. 4 and 5. Table 1 shows the increase in lead inductance relative to a lead without magnetically impregnated insulative layers (i.e., the ratio of a lead with magnetically impregnated insulative layers to a lead without magnetically impregnated insulative layers), as a function of the $\mu_r$ and percentage of magnetic material by volume in the insulative layers 65, 68.

TABLE 1

Relative increase in lead inductance

| $\mu_r$ of Magnetic Material | Percentage of magnetic material in insulative layers | | | |
| --- | --- | --- | --- | --- |
| | 1% | 10% | 25% | 50% |
| 10 | 1.0 | 1.0 | 1.7 | 2.8 |
| 100 | 1.0 | 5.0 | 12 | 23 |
| 1,000 | 5.0 | 45 | 110 | 220 |
| 10,000 | 45 | 440 | 1,100 | 2,200 |
| 100,000 | 440 | 4,400 | 11,000 | 22,000 |

In some embodiments, one or both of the insulative layers 65, 68 may be impregnated with a radiopaque material that assists locating the lead 14 during implantation and extraction.

Figure 4:
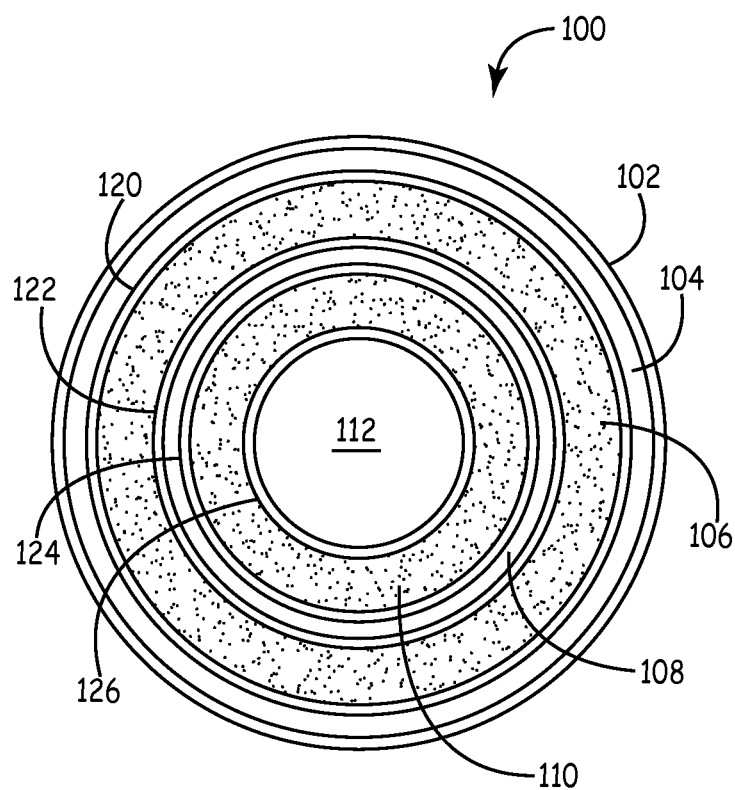
FIG. 4 is a cross-section view of an embodiment of a lead including magnetically impregnated insulative layers with adjacent non-magnetically impregnated insulative layers.

FIG. 4 is a cross-section view of a lead 100 according to another embodiment. The lead 100 may be employed in place of or in addition to the leads 14, 16 shown in FIG. 1. The lead 100 includes an insulative lead body 102, an outer conductive coil 104, an outer magnetically impregnated insulative layer 106, an inner conductive coil 108, and an inner magnetically impregnated insulative layer 110. In this embodiment, the outer magnetically impregnated insulative layer 106 is disposed between the outer conductive coil 104 and inner conductive coil 108, and the inner magnetically impregnated insulative layer 110 is disposed between the inner conductive coil 108 and a central lumen 112 of the lead 100. Alternatively, the magnetically impregnated insulative layers 106, 110 may surround the conductive coils 104, 108, respectively. The conductive coils 104, 108 and magnetically impregnated insulative layers 106, 110 may have configurations and variations similar to related elements described herein with regard to FIG. 3.

The lead 100 further includes non-magnetically impregnated insulative layers 120, 122, 124, 126 that are located adjacent to the magnetically impregnated insulative layers 106, 110. Particularly, non-magnetically impregnated insulative layer 120 is between the outer conductive coil 104 and the magnetically impregnated insulative layer 106, non-magnetically impregnated insulative layer 122 is between the magnetically impregnated insulative layer 106 and the inner conductive coil 108, non-magnetically impregnated insulative layer 124 is between the inner conductive coil 108 and the magnetically impregnated insulative layer 110, and the non-magnetically impregnated insulative layer 126 is between the magnetically impregnated insulative layer 110 and the central lumen 112. As a result, the magnetically impregnated insulative layers 106, 110 are isolated from adjacent structures by non-magnetically impregnated insulators. As discussed above, it may be desirable to isolate the magnetically impregnated insulative layers 106, 110 from other electrical or magnetic structures in the lead 100, especially with increased percentages of magnetic material in the insulative layers 106, 110.

Figure 5:
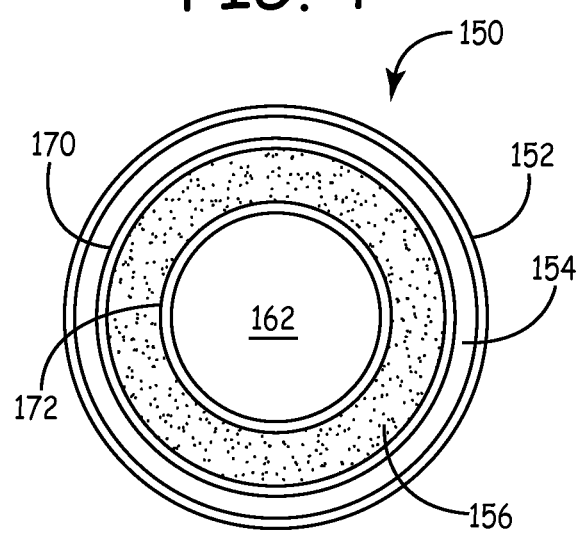
FIG. 5 is a cross-section view of an embodiment of a lead including a single lead conductor and a magnetically impregnated insulative layer with adjacent non-magnetically impregnated insulative layers.

FIG. 5 is a cross-section view of a lead 150 according to another embodiment. The lead 150 may be employed in place of or in addition to the leads 14, 16 shown in FIG. 1. The lead 150 includes an insulative lead body 152, a conductive coil 154, and a magnetically impregnated insulative layer 156. Thus, in this embodiment the lead 150 includes a single conductive element. The magnetically impregnated insulative layer 156 is disposed between the conductive coil 154 and a central lumen 162 of the lead 150. Alternatively, the magnetically impregnated insulative layer 156 may surround the conductive coil 154, respectively. The conductive coil 154 and magnetically impregnated insulative layer 156 may have configurations and variations similar to related elements described herein with regard to FIG. 3.

The lead 150 further includes non-magnetically impregnated insulative layers 170, 172 that are located adjacent to the magnetically impregnated insulative layer 156. Particularly, non-magnetically impregnated insulative layer 170 is between the conductive coil 154 and the magnetically impregnated insulative layer 156, and the non-magnetically impregnated insulative layer 172 is between the magnetically impregnated insulative layer 156 and the central lumen 162. As a result, the magnetically impregnated insulative layer 156 is isolated from adjacent structures by non-magnetically impregnated insulators. As discussed above, it may be desirable to isolate the magnetically impregnated insulative layer 156 from other electrical or magnetic structures in the lead 14, especially with increased percentages of magnetic material in the insulative layers 156.

Various modifications and additions can be made to the exemplary embodiments discussed without departing from the scope of the present invention. For example, while the embodiments described herein refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical device lead comprising:
    a proximal end configured to couple the lead to a medical device;
    an insulative lead body extending distally from the proximal end;
    a first conductor coil coupled to the proximal end and extending through the lead body, the first conductor coil coupled to a first electrode at a distal end of the first conductor coil, the first conductor coil having a first inner lumen; and
    a first magnetically impregnated polymer layer adjacent the first conductor coil and extending within the first inner lumen of the first conductor coil, the first magnetically impregnated polymer layer configured to increase the self inductance of the first conductor coil to reduce RF energy absorption.

2. The medical device lead of claim 1, and further comprising:
    a second conductor coil coupled to the proximal end and extending coaxially within the first inner lumen of the first conductor coil, the second conductor coil coupled to a second electrode at a distal end of the second conductor coil, the second conductor coil having a second inner lumen; and
    a second magnetically impregnated insulative layer adjacent the second conductor coil and extending within the second inner lumen.

3. The medical device lead of claim 1, wherein the first magnetically impregnated polymer layer contains particles of magnetic material having a minimum diameter of about 0.5 mm or greater.

4. The medical device lead of claim 1, wherein a percentage of magnetic material in the first magnetically impregnated insulative layer is less than or equal to about 10%.

5. The medical device lead of claim 1, wherein the first magnetically impregnated insulative layer comprises particles of magnetic material having at least one of varying sizes and varying shapes.

6. The medical device lead of claim 5, wherein the particles of magnetic material are nanoparticles.

7. The medical device lead of claim 1, wherein the first magnetically impregnated insulative layer comprises magnetically impregnated sections spaced apart by non-magnetically impregnated sections that provide impedance discontinuities in the first magnetically impregnated insulative layer.

8. A medical device lead comprising:
    an insulative lead body;
    a first lead conductor extending through the lead body, the first lead conductor coupled to a first electrode at a distal end of the first lead conductor, the first lead conductor coiled to have a first inner lumen; and
    a first magnetically impregnated insulative layer between the first lead conductor and a central lumen of the medical device lead, the first magnetically impregnated insulative layer extending within the first inner lumen of the first lead conductor and configured to increase the self inductance of the first coiled conductor to reduce RF energy absorption.

9. The medical device lead of claim 8, and further comprising:
    a first non-magnetically impregnated insulative layer between the first magnetically impregnated insulative layer and the central lumen; and
    a second non-magnetically impregnated insulative layer between the first lead conductor and the first magnetically impregnated insulative layer.

10. The medical device lead of claim 9, and further comprising:

a second lead conductor extending coaxially with the first lead conductor, the second lead conductor coupled to a second electrode at a distal end of the second lead conductor.

11. The medical device lead of claim 10, and further comprising:
a second magnetically impregnated insulative layer between the first lead conductor and the second non-magnetically impregnated insulative layer, wherein the second lead conductor is coiled to have a second inner lumen and the second magnetically impregnated insulative layer extends within the second inner lumen.

12. The medical device lead of claim 11, wherein the first magnetically impregnated polymer layer contains particles of magnetic material having a minimum diameter of about 0.5 mm or greater.

13. The medical device lead of claim 8, wherein the first magnetically impregnated insulative layer comprises particles of magnetic material.

14. The medical device lead of claim 13, wherein the particles of magnetic material are substantially spherical.

15. The medical device lead of claim 13, wherein the particles of magnetic material have varying sizes and/or varying shapes.

16. The medical device lead of claim 8, wherein the first magnetically impregnated insulative layer comprises magnetically impregnated sections spaced apart by non-magnetically impregnated sections that provide impedance discontinuities in the first magnetically impregnated insulative layer.

17. A medical device, comprising:
a pulse generator; and
a lead couplable to the pulse generator and including a lead body, an outer conductive coil extending through the lead body, and an inner conductive coil extending coaxially with the outer conductive coil, the lead further including a first insulative layer between the inner conductive coil and a central lumen of the lead, and a second insulative layer between the inner conductive coil and outer conductive coil, wherein at least one of the first and second insulative layers includes a magnetic material configured to increase the self inductance of the outer conductive coil to reduce RF energy absorption.

18. The medical device of claim 17, wherein the lead further comprises:
a third insulative layer between the first insulative layer and the central lumen; and
a fourth insulative layer between the inner conductive coil and the first insulative layer.

19. The medical device of claim 18, wherein the lead further comprises:
a fifth insulative layer between the first lead conductor and the second insulative layer; and
a sixth insulative layer between the second insulative layer and the second lead conductor.

20. The medical device of claim 17, wherein the magnetic material comprises particles having a minimum diameter of about 0.5 mm or greater.

* * * * *